United States Patent [19]

Ashmead et al.

[11] Patent Number: 4,863,898

[45] Date of Patent: Sep. 5, 1989

[54] AMINO ACID CHELATED COMPOSITIONS FOR DELIVERY TO SPECIFIC BIOLOGICAL TISSUE SITES

[75] Inventors: Harvey H. Ashmead, Kaysville; H. Dewayne Ashmead, Fruit Heights; Darrell J. Graff, Ogden, all of Utah

[73] Assignee: Albion International, Inc., Clearfield, Utah

[21] Appl. No.: 826,786

[22] Filed: Feb. 6, 1986

[51] Int. Cl.$^4$ .................. A61K 37/02; A61K 31/555; A61K 31/28; A61K 31/315
[52] U.S. Cl. .......................................... 514/6; 514/18; 514/19; 514/21; 514/494; 514/880; 514/891; 514/893; 514/492; 514/499; 514/500; 514/501; 514/502; 514/505; 514/419; 514/428; 514/399
[58] Field of Search ...................... 514/494, 6, 18, 19, 514/880, 893, 891, 419, 428, 399; 424/94, 103, 105, 106, 108, 110, 111

[56] References Cited

U.S. PATENT DOCUMENTS

| | | | |
|---|---|---|---|
| 3,887,704 | 6/1975 | Lichtenstein | 514/494 |
| 4,020,158 | 4/1977 | Ashmead et al. | 514/6 |
| 4,167,564 | 9/1979 | Jensen | 514/6 |
| 4,172,072 | 10/1979 | Ashmead | 435/272 |
| 4,599,152 | 7/1986 | Ashmead | 204/72 |

FOREIGN PATENT DOCUMENTS 3026368 2/1982 Fed. Rep. of Germany .
0216122 12/1983 Japan .
2052978A 2/1981 United Kingdom .

OTHER PUBLICATIONS

Frost, *Science Counselor,* Jun. 1956.
Rabin, *Trans Farady Society,* 52, 1130–1136 (1956).
Perkins, *Biochem. Journal,* 57, 702–704 (1954).
Bossu, *J. Am. Chem. Soc.,* 99, 2195–2203 (1977).
Martin, *J. Am. Chem. Soc.,* 82, 495–498 (1960).

*Primary Examiner*—Howard E. Schain
*Assistant Examiner*—F. T. Moezie
*Attorney, Agent, or Firm*—Thorpe, North & Western

[57] ABSTRACT

Amino acid chelates having a ligand to divalent metal mole ratio of at least 2:1 and having a molecular weight of not more than 1500 and preferably not more than 1000 and also having a stability constant of between about 10 and 10 are formulated for delivery to one or more specific tissue sites within a mammal. The ligand utilized in formulating the amino acid chelate is a naturally occuring amino acid or a dipeptide, tripeptide or quadrapeptide thereof. The selection of an appropriate ligand with which to form the chelate provides a product that, when entering the bloodstream of the mammal, either by mean of oral ingestion or injection, has a propensity to migrate to one or more targeted tissue sites within the mammal.

21 Claims, No Drawings

AMINO ACID CHELATED COMPOSITIONS FOR DELIVERY TO SPECIFIC BIOLOGICAL TISSUE SITES

BACKGROUND OF THE INVENTION

This invention relates to amino acid chelated compositions which are formulated for delivery to one or more specific tissue sites within a living organism. More specifically, this invention relates to compositions consisting of selected mineral cations chelated with selected amino acid or peptide ligands. These chelates are absorbed intact into biological tissues and, because of either the selected ligands or the ligands chelated to certain metals, migrate to specific tissue target sites within a living organism where the chelate is utilized as is or is dissociated into mineral cations and amino acids or peptides for utilization at that site.

Amino acid chelates are becoming well accepted as a means of increasing the metal content in biological tissues of man, animals and plants. By amino acid chelates is meant the product resulting from the reaction of a polypeptide, dipeptide or naturally occuring alpha amino acid with a metal ion having a valence of two or more to form a ring structure wherein the positive electrical charges of the metal ion are neutralized by the electrons available through the carboxylate or free amino groups of the alpha amino acid. Chelate formation through neutralization of the positive charges of the divalent metal ions can be through the formation of ionic, covalent or coordinate covalent bonding. In the past, amino acid chelates have generally been made by first dissolving a water soluble divalent metal salt in water. An amino acid ligand is then reacted with the metal ion at a ratio of ligand to metal of at least 2:1. In order for the reaction to proceed to completion, the amino acid has had to be at a pH which is preferably above or more basic than the isoelectric point of the amino acid. This procedure generally results in a a chelate containing a certain amount of inorganic anion radicals such as sulfates, chlorides and the like. In Ashmead, U.S. Pat. No. 4,599,152, issued July 8, 1986 pure amino acid chelates free of inorganic anion radicals and a method for their preparation is taught. The present invention encompasses the use of both pure amino acid chelates and those containing inorganic anion radicals. However, the use of pure amino acid chelates is preferred.

For convenience sake, metal ions having a valence of two or more will simply be referred to as divalent metal ions or divalent cations. Hence, the ferric ion $Fe^3$ is considered to be a divylent ion for purposes of this specific cation. For the same reasons, naturally occurring alpha amino acids will be referred to as amino acids. Although the term amino acid as used throughout this specification refers only to products obtainable through the hydrolysis of proteins, that does not mean that synthetically produced amino acids are to be excluded provided they are the same as can be obtained through the hydrolysis of proteins. Therefore, protein hydrolysates such as quadrapeptides, tripeptides, dipeptides and naturally occuring alpha amino acids may collectively be referred to as amino acids. These amino acids are important building blocks for proteins and function as such when ingested into biological tissues.

Amino acid chelates are sufficiently stable, when properly formulated, that they are absorbed intact into biological systems where the chelate is transported to the site of utilization. At that site, the chelate may be utilized intact or the chelate bonding may be broken and the metal ion and amino acids utilized by the system. In mammals, for example, small intestine. Properly formulated amino acid chelates have been found to have stability constants which are sufficient to hold the chelate intact while it is absorbed into, the blood. Once absorbed, it is transported intact via a dipeptide transport mechanism to a specific site within the system where the metal ion and amino acid ligand portions are then utilized as needed.

Exemplary of the prior art teaching the use of amino acid chelates for uptake into biological systems are Ashmead, U.S. Pat. No. 4,076,803, issued Feb. 28, 1978 for "Synergistic Combination of Metal Proteinates With Beta-Chlorovinyl Dialkyl Phosphates"; Ashmead, U.S. Pat. No. 4,103,003 issued July 25, 1978 for "Composition for Improving Biologic Development"; Ashmead, U.S. Pat. No. 4,19,716 issued Oct. 2, 1979 for "Synergistic Metal Proteinate Plant Hormone Compositions"; Ashmead, U.S. Pat. No. 4,169,717 issued Oct. 2, 1979 for "Synergistic Plant Regulatory Compositions"; Ashmead, U.S. Pat. No. 4,172,072 issued Oct. 23, 1979 for "Buffered Enzymatically Produced Metal Proteinates"; Ashmead, U.S. Pat. No. 4,201,793 issued May 6, 1980 for "Oil Cooked Foods Containing Metal Proteinates"; Ashmead, U.S. Pat. No. 4,216,143 issued Aug. 5, 1980 for "Soluble Non-Ferrous Metal Proteinates"; Ashmead, U.S. Pat. No. 4,216,144 issued Aug. 5, 1980 for "Soluble Iron Proteinates"; Ashmead et al, U.S. Pat. No. 3,873,296 issued Mar. 25, 1975 for "Increasing Metal in Biological Tissue"; Ashmead et al, U.S. Pat. No. 4,020,158 issued April 26, 1977 for "Increasing Metal in Biological Tissue"; Jensen, 3,969,540 issued July 13, 1976 for "Enzymatically prepared Metal Proteinates; and Jensen, 4,167,564 issued Sept. 11, 1979 for "Biological Assimilation of Metals".

While the above cited art teaches that amino acid chelates (also sometimes referred to as metal proteinates) are effective in increasing metal content in biological tissue such use is nondiscriminatory in that the increase in metal content is generally "across the board" in all tissues. While such useage is generally beneficial to an organism which is deficient in certain metals, there are also occasions where it is desirable to have a metal ion migrate or be targeted to a certain tissue site within a biological organism. For example, calcium is essential in the growth and repair of bones and teeth. It is also necessary to normal heart functioning, nerve irritability and clotting of blood. Magnesium is also essential to the bones as well as in the liver and certain muscles. Magnesium also aids in the transfer of intercullar water by osmosis, is a catalyzer for some enyzme reaction and in energy production. Copper is needed in combination with iron to build hemoglobin, is necessary for the production of RNA and aids in the development of bones, brains, connective tissue and pigment formation. Zinc is found in liver, bones, epidermal tissues, blood, pancreas, kidneys, and pituitary glands. Also, zinc has been linked to synthesis of protein, as a constituent of insulin, as a constituent in carbohydrate metabolism and aids in healing of wounds. Manganese is a component in activating numerous enzymes such as peptidases, phosphatases, arginase, cozymase, carboxylase and cholinesterase, which aid in digestion, metabolism of carbohydrates, protein and fat. Manganese is stored primarily in the kidney and liver. Other metals capable of being chelated, which also have important biological functions, are chromium, cobalt, molybdenum and selenium.

Certain of nutritional supplements have been marketed consisting of glandular materials allegedly chelated with metal cations. It has been stated that when a metal ion is chelated with a glandular material and ingested into an animal or human being, the glandular material chelate enhances the function of that particular organ, the glandular material was obtained from. While this thesis may sound logical, it is based on the premise that glandular materials are absorbed intact rather than being digested prior to being absorbed. It is well known that most proteins are not absorbed intact. Rather, they are broken down into single amino acids or at best small peptide chains before intestinal absorption can take place. Insulin, for example, cannot be given orally. As compared to insulin, oral hypoglycemic agents are low molecular weight sulfonamides such as tolbutamide, tolazamide or chlorpropamide which are not digested prior to being absorbed through the gut. It, therefore, follows that one ingesting raw processed pancreas will not reap the benefit of any insulin contained therein. The same reasoning may be applied to other bioactive proteins contained in other glandular materials.

OBJECTS AND SUMMARY OF THE INVENTION

It is object of the present invention to provide an amino acid chelate composition which, when ingested into a living organism, will be transported to one or more targeted sites within that organism such as muscle, endocrine glands, adipose tissue, reproductive organs, blood cells, brain tissues and enzyme systems.

Another object of the present invention is to provide a means of delivering a specific mineral ion to a targeted site within a living organism through utilization of a dipeptide-like transport system.

Still another object of this invention is to provide an amino acid chelated composition capable of being absorbed as an intact molecule into a biological organism and be transported to a selected tissue site.

These and other objects may be accomplished by means of an amino acid chelate formed by the reaction of selected divalent metal cations with selected amino acid ligands. The ligands are those which have a propensity to be transported to a specific tissue site. These amino acid chelates are absorbed intact through the intestinal tract via active dipeptide transport and are protected from dipeptidase activity by the presence of the mineral in the chelate. To help insure the stability of the chelate in the harsh environment of the stomach and intestines, the ligand to mineral divalent cation ratio must be at least 2:1 and the molecular weight must not exceed 1500 and preferably will not exceed 1000. In order for the chelate to pass through the acddic media of the stomach, the chelate must also have a stability constant on the order of $10^6$ to $10^{12}$.

Such amino acid chelates are absorbed intact into the mucosal cells and move, also intact, into the portal bloodstream where they are, because of their ligand makeup, transported to certain tissue sites. Upon reaching a selected site, they are either utilized intact or disassociated into mineral cations and free amino acids or dipeptides for utilization. The exact reason for these types of chelates being transported to a specific site is not know for a surety. It is believed that the ligands have a propensity for movement to a specific tissue site. However, it could also be that the reason for the targeting is due to a need at the tissue site for both the ligand and the metal. Therefore, the intact chelate may be the key to transport to a specific site and also to entering into the biochemical reaction at that site as an intact molecule.

DETAILED DESCRIPTION OF THE INVENTION

It has been documented that mineral absorption from the intestinal tract occurs via at least two pathways. A mineral salt, after ingestion is solubilized and ionized in the acid pH of the stomach. The metal cations passing from the stomach into the intestinal tract are absorbed, if at all, in the duodenum or upper portion of the intestine. This requires a relatively low pH. It is believed that the metal cation is presented to the integral proteins in the brush border of mucosal cells of the duodenum. The transport of the metal ion across the mucosal cell membrane is accomplished by chelating the cation to complex carrier proteins. This binding commences the activation of an enzymatic system called a "pump". Several enzyme reactions occur in which the cation is moved from enzyme to enzyme within the system. This movement is very rapid and stops when the cation is delivered to the interior side of the mucosal membrane where the metal cation is released and rechelated by cytoplasmic proteins, such as apoferritin, in the case or iron or transmaganin in the case of magnesium. The cation chelated with cytoplasmic protein is then carried to the plasma.

Metal ions absorbed in this manner are reacted, released, re-reacted and re-released repeatedly during their transport from the intestinal tract to the portal blood.

Metal cations which are not absorbed via the duodenum descend on through the intestine where the pH is increased. As pH increases, the metal ions react with phytates, phosphates hydropides and other anions and form precipitates. These precipitates are not soluble and pass through the gut and are excreted unabsorbed in the feces.

It has also been documented that when an impermeant substance, such as a metal ion is chemically linked to a low molecular weight peptide, that the resultant complex can be transported intact via a peptide permease across the cell membrane. This has been referred to as having the impermeant substance "smuggled" across the membrane and the complex has accordingly been referred to in the literature as a "smugglin". Thus, metal ions reacted with two or more low molecular weight amino acid or dipeptide, tripeptide or quadrapeptide ligands to form an amino acid chelate having a molecular weight of no more than about 1500 and having a stability constant of between about $10^6$ to $10^{12}$ may be absorbed and transported or "smuggled" intact across the mucosal cell membrane and into the portal blood as if they were dipeptides in the presence of a cation.

The formation of a dipeptide like chelate is indicated by the following formula:

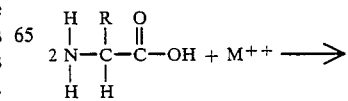

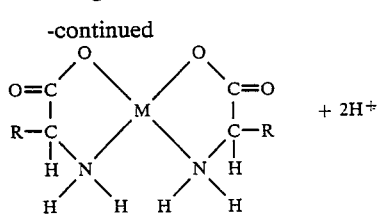 + 2H⁺ where R is hydrogen, alkyl or any other alpha amino acid or dipeptide, tripeptide or quadrapeptide moiety and M++ is a divalent metal cation of a metal selected from the group consisting of calcium, magnesium, manganese, iron, copper and zinc. In addition, any other cation considered to be biologically necessary such as cobalt, chromium, molybdenum or selenium may also be utilized. Thus, R may be any radical such that the reacting ligand is a naturally occuring alpha amino acid selected from the group consisting of alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine and valine or dipeptides, tripeptides or quadrapeptides formed by any combination of the above. Each chelated metal ion will contain at least two ligands forming two heterocyclic rings but may, in certain instances, contain up to four ligands forming at least two to four heterocyclic rings depending upon the coordination number of the ion. For example, magnesium, copper, calcuim and iron are more likely to be more stable at a ligand to metal mole ratio of 2:1 whereas zinc and manganese are more likely to have ligand to metal mole ratios of 3:1.

The limiting factor of each dipeptide like amino acid chelate formed is that the molecular weight must not exceed about 1500 and the stability constant must be within the range of about $10^6$ to $10^{12}$. The more ligands forming heterocyclic rings the higher the stability constant will be. Preferably, the molecular weight will not exceed 1000 and the ligand will not be greater than a tripeptide. Most preferably, the molecular weight will not exceed 500.

The determination of stability constants of amino acid chelates is well documented in U.S. Pat. No. 4,167,564 and the means by which amino acid chelates may be formulated to provide optimal stability constants within the required ranges are disclosed in U.S. Pat. Nos. 4,176,564 and 4,172,072.

Manganese, calcium, iron, magnesiuim and copper amino acid chelates seem to perform best at stability constants of about $10^{10}$ whereas zinc amino acid chelates appear to perform best as lower ranges of about $10^7$ to $10^9$.

The intact absorption of dipeptide like amino acid chelates is also well documented by Ashmead, Graff and Ashmead, Intestinal Absorption of Metal Ions and Chelates, Charles C. Thomas Publisher, Springfield, Ill., 1985.

Once dipeptides and/or amino acids are absorbed into the portal blood, they pass to the liver and then into general circulation. Intact dipeptide-like amino acid chelates are believed to follow a different pathway once in the blood. Some may be hydrolyzed in the mucosal cells prior to being passed to the portal blood and some may be utilized by the liver to form plasma proteins. However, those that survive and pass intact into the bloodstream find their way directly to the tissue for which they are needed, since each tissue is capable of synthesizing its own protein.

Therefore, it has been found that if a dipeptide-like amino acid chelate is formed from amino acid or dipeptide, tripeptide or quadrapeptide ligands having a propensity for use at a particular tissue site and a metal cation also needed at that site, those ligands can selectively "smuggle" or transport that metal cation directly to that tissue site.

The tissue sites, metals and ligands are too numerous to specifically enumerate in this disclosure and may be determined empirically by one skilled in the art from the teachings contained herein. Leucine is a dominant amino acid in muscle, kidney, adipose and brain tissues. Glycine is primary in the synthesis of heme. Arginine is important in male reproductive organs. The hormone TRH (thyropin-releasing-hormone), is the tripeptide glutamic acid-histidine-proline.

The following table enumerates those tissue sites considered to be most pertinent and the ligands and metals which may be targeted to those sites in the form of the amino acid chelate compositions of this invention.

| TISSUE SITE | METAL IONS(S) | LIGAND(S) |
| --- | --- | --- |
| Brain | Zinc | Phenylalanine |
|  | Magnesium | Tryptophan |
|  | Calcium | Leucine |
|  |  | Arginine |
|  |  | Glumatic Acid |
|  |  | Tryocine |
|  |  | Serine |
|  |  | Cysteine |
|  |  | Mathionina |
| Hypothalamus | Calcium | Glycine |
|  | Zinc | Glutamic Acid |
|  | Manganese | Histidine |
|  |  | Proline |
|  |  | Arginine |
| Pituitary | Calcium | Glycine |
|  | Zinc | Phenylalanine |
|  | Manganese | Glutamic Acid |
|  |  | Histidine |
|  |  | Proline |
|  |  | Arginine |
|  |  | Ornithine |
|  |  | Lysine |
| Heme | Iron | Glycine |
|  | Copper | Histidine |
| Ovaries | Magnesium | Methionine |
|  | Manganese | Leucine |
| Skin and Hair | Zinc | Methionine |
|  |  | Cystine |
|  |  | Cysteine |
|  |  | Leucine |
| Testes | Zinc | Arginine |
|  | Copper |  |
| Epididymus | Zinc | Arginine |
|  |  | Glycine |
| Seminal Vesicle | Zinc | Arginine |
|  |  | Glycine |
| Liver | Iron | Leucine |
|  | Zinc | Arginine |
|  | Copper | Methionine |
|  | Manganese | Cystine |
|  |  | Cysteine |
|  |  | Lysine |
|  |  | Glycine |
|  |  | Histidine |
| Kidney | Iron | Lysine |
|  | Zinc | Arginine |
|  | Copper | Methionine |
|  | Manganese | Leucine |
| Thyroid | Zinc | Phenylalanine |
|  |  | Glutamic Acid |
|  |  | Histidine |
|  |  | Proline |

| TISSUE SITE | METAL IONS(S) | LIGAND(S) |
|---|---|---|
| Skeletal Muscles | Calcium<br>Magnasium | Glycium<br>Tryptophan<br>Valine<br>Arginine |
| Heart | Iron<br>Magnesium<br>Calcium | Leucine<br>Aspartic Acid |
| Pancreas | Zinc<br>Calcium | Leucine<br>Arginine<br>Glycine<br>Tryptophan |
| Bones and Teeth | Calcium<br>Magnasium | Lysine |
| Enzyme System | Chromium<br>Calcium<br>Magnesium<br>Zinc<br>Iron<br>Copper<br>Manganese<br>Cobalt<br>Molybdenum | Leucine |
| Nucleic Acids | Magnesium | Glutamic Acid<br>Glutamine<br>Glycine<br>Aspartic Acid |
| Wounds | Zinc | Methlonine<br>Arginine |

From the above listed metals and ligands, numerous chelates are demonstrated in the following examples to be effective in either being absorbed through the intestinal tract of a mammal and transported to a specific tissue site or being injected into the bloodstream of an animal and transported to a specific tissue site. Preferably, the amino acid chelates will be administered orally; however, injection into the bloodstream or other body tissues or fluids is not to be precluded. The exact amount of mineral to be administered in the form of the ligand specific amino acid chelates may be empirically determined according to need. In those minerals for which the U.S. government has determined a recommended daily allowance (U.S. RDA) for human beings, the amount of mineral need not, in most instances, exceed that amount. For those minerals for which a U.S. RDA has not been determined, the amount will be governed according to need. These minerals are usually needed in trace amounts only and dosages will be administered accordingly. However, for larger animals, such as represented by the bovine and equine species, much larger amounts may be administered. Hence, the term "effective amount" may vary from species to species, and will be obvious to those skilled in the art according to the particular animal species. The amino acid chelates can be administered separately, as a combination of different metal chelates containing different ligands, or admixed with other ingredients including fillers, excipients, vitamins and other foodstuffs. When orally administered, they may be utilized in the form of capsules, tablets, powders, syrups, elixers or any other suitable form.

The following examples are representatvie of the invention. Unless otherwise specified, all amino acids utilized, with the exception of glycine which contains no asymmetric atom, are the "L" or levo form as that is the natural form of amino acids obtained from the hydrolysis of proteins.

EXAMPLE I

A calcium glycine amino acid chelate was formed by reacting two moles of glycine per mole of radioactive calcium and was compared with a calcium chloride salt also containing radioactive calcium. The calcium glycine chelate had a molecular weight of 198 and had a stability constant of $10^{10}$. Six female rats, weighing 250 gms.±10 gms., were divided into two groups. All rats were anethetized with 0.15 mls sodium phenobarbital USP. To three rats was administered 0.06 mg Ca containing 12.5 micro curies of radioactive calcium as the calcium glycine amino acid chelate by intravenous injection. To the other three, the same amount of calcium was administered in the form a calcium chloride.

After two hours, all of he rats were sacrificed and the hypothalamus was removed and read for radioactivity. The rats receiving the inorganic calcium showed a mean value of 67.1±8.4 corrected counts per minute per milligram of tissue (cc/min/mg) as compared with a mean value of 94.5±22.9 cc/min/mg for the rats receiving the chelated calcium. This in an increase of 39.6%. The uterus, skeltal muscles and pituitary were also examined and in each case the group receiving the chelate showed an increase in calcium uptake. However, the uptake was much lower as compared with the hypothalamus showing that the glycine and calcium combined had a preference for being transported to the hypothalmus.

EXAMPLE II

The amino acid, arginine, is a dominant amino acid in the well being of the male sex organs. To a lesser extent, glycine also plays a role in the functioning of these organs. The metal, zinc, is also a dominant ingredient for the proper functioning of these organs.

This example shows the effectiveness of administering amino acid chelated zinc to rats utilizing as ligands arginine and glycine at a ligand to metal mole ratio of 2:1.

A zinc-arginine chelate was made having a molecular weight of 412.2 and a stability constant of $10^7$. Similarly, a zinc-glycine chelate havi g a molecular weight of 213.5 and a stability constant of $10^7$.

Three groups of rats, six in each group, weighing 250 gms±10 gms. were given an intravenous dosage, of 0.06 mg zinc containing 10 microcuries of radioactive zinc. Group I received the zinc chelated with the arginine, Group II receive the zinc chelated with glycine and Group III received the same amount of zinc as a zinc chloride salt.

Each rat was sacrificed 24 hours post treatment and the testes, epididymis, and seminal visicle of each were exposed, excised and a determination was made of the amount of radioactive zinc in each. The radioactive counts were averaged for each group and are reported as corrected counts per minute per milligram of tissue (cc/min/mg) in the following table.

| TISSUE | GROUP I | GROUP II | GROUP III |
|---|---|---|---|
| Testes | 1.26 | .96 | Negligible |
| Epididymis | 1.03 | .73 | Negligible |
| Seminal Vesicle | 2.53 | 1.98 | Negligible |

The above data show the propensity of the zinc-arginine chelate, and to a lesser extent the zinc-glycine chelate, for migration to the reported male sex tissues as compared to the same amount of zinc administered as zinc chloride.

EXAMPLE III

This example, as in the case of Examples I and II above, is based on the premise that the amino acid chelate utilized will be absorbed intact through the intestinal tract and into the blood stream. Hence, in order to expedite transport from the blood to specific tissue sites the chelate was injected direrctly into the jugular vein of the rats used for the experiment.

Twelve female rats of comparable weight were dosed with either a manganese amino acid chelate or a manganese chloride salt. In either case, the dosage consisted of 5.2 mcg of manganese, containing 10 mico curies of radioactive manganese. The manganese amino acid chelate was made utilizing a tripeptide of proline, histidine and glutamic acid as ligands and the mole ratio, of tripeptide ligand to manganese was 2:1. The chelate had a mole weight of 886 and a stability constant of $10^7$.

In performing the experiment, the rats were anethetized with sodium phenobarbital USP (30 mg/kg) and the radioactive manganese preparation was injected into the jugular vein with six rats receiving the amino acid chelate and six receiving the manganese chloride salt.

One hour after injection, three animals from each group were sacrificed. The remaining three from each group were sacrificed two hours after injection. The hypothalamus, pituitary and uterus of each animal was exposed and excised. The excised tissues were then tested for radioactivity and the mean counts of group of each three were reported as corrected counts per minute per milligram of tissue (cc/min/mg). The results are reported in the following table:

| Tissue | MgCl Salt 1 hr | MgCl Salt 2 hr | Mg Chelate 1 hr | Mg Chelate 2 hr |
|---|---|---|---|---|
| Pituitary | 100 | 100 | 125 | 150 |
| Uterine | 50 | 50 | 100 | 100 |
| Hypothalamus | 25 | 25 | 50 | 25 |

It will be noted that in the manganese salt group there was no noticable change in manganese concentration in the hypothalamus or pituitary from one hour to two hours time. In the chelated group, there was a very interesting change in that, at the end of two hours, the manganese concentration had dropped by 25 cc/min/mg in the hypothalamus tissues and increased by the same amount in the pituitary tissue indicating that the chelate initially carried the metal to the hypothalamus, which in turn was better able to utilize the mineral and transfer it on to the pituitary. Although there was no appreciable change in the uterine endometrial tissue when utilizing the chelate, the mineral absorption from the chelate into the uterine tissues was twice as great as from the manganese chloride salt.

EXAMPLE IV

The method of Example III was again utilized except that the manganese was replaced by zinc. The ligand to zinc ratio was 2:1. The zinc amino acid chelate had a molecular weight of 896 and a stability constant of $10^7$. The same dosage as in Example III was administered. Only six rats were utilized for this experiment, three in each group, and they were sacrificed two hours post injection into the jugular vein. Six tissues, i.e. brain, skeletal muscle, liver, hypothalamus, pituitary and uterus were analyzed for radioactive zinc with the following mean results for each group reported in terms of cc/min/mg of tissue.

| Tissue | Zinc Chloride | Zinc Chelate |
|---|---|---|
| Brain | 5.1 | 5.9 |
| Skeletal Muscle | 5.2 | 6.1 |
| Liver | 94.2 | 178.3 |
| Hypothalamus | 3.0 | 17.3 |
| Pituitary | 17.0 | 56.4 |
| Uterus | 14.0 | 27.2 |

The above results confirm those in Example III showing the preference of the chelated zinc fpr migration to the hypothalamus and pituitary glands. The absorption into the liver and uterus was also significant. There was an increase in zinc in the brain and skeletal tissues which, had the experiment continued for longer than two hours, might have shown more significance.

EXAMPLE V

This example shows the effectiveness of forming a chelate of the metal and ligand in a 2:1 ligand to metal ratio as compared to administering the same metal and ligand in the form of a 1:1 ligand to metal ratio or as an unreacted mixture or utilizing 2 moles of the ligand admixed with 1 mole of a metal salt. Leucine was used as the ligand and zinc as the metal. Composition A is therefore a mixture, or at best a complex consisting of one mole of leucine (mole weight 131.17) and one more of zinc chloride. The pH of Composition A was adjusted to 9 to be comparable with Composition C. Composition B consisted of two moles of leucine admixed with one mole of zinc chloride to form a mixture. Composition C was formed by reacting two moles of leucine with one mole of zinc to obtain a zinc-leucine amino acid chelate having a molecular weight of about 325.82. At a pH of 9, this chelate had a stability constant of 10.

The rats used in this experiment were each dosed with a solution of the stated composition to provide an amount of zinc equivalent to 10 microliters of 0.073M $ZnCl_2$ containing 9.2 microcuries of radioactive zinc. Composition A contained leucine equivalent to 10 microliters of 0.76M. leucine and was adjusted to pH 9 with 20 microliters of 0.05 N NaOH. Composition B contained leucine equivalent to 20 microliters of 0.76M. leucine containing 20 microliters distilled water in lieu of pH adjustment. The pH of this solution was about 3. Composition C contained the same ingredients as Composition B except in chelated form and the pH was adjusted to 9 with 20 microliters of 0.13M $Na_2 CO_3$.

The procedure of Example II was fo lowed using three rats in each group. Upon sacrificing, blood was drawn and certain tissues excised to determine the amount of radioactive zinc which had migrated to the blood and tissues two hours post injection. The results are expressed as corrected counts per minute per milligram of tissue (cc/min/mg) in the following table:

| Tissue | Comp. A | Comp. B | Comp. C |
|---|---|---|---|
| Blood | 0.90 | 1.31 | 1.64 |
| Liver | 5.15 | 6.20 | 8.65 |
| Kidney | 5.45 | 6.46 | 8.55 |
| Heart | 6.42 | 5.23 | 6.32 |
| Muscle | 2.41 | 3.10 | 3.88 |
| Brain | 1.22 | 3.86 | 2.41 |
| Total | 21.55 | 26.16 | 31.45 |

The amount of zinc from Composition C (chelate) appearing in the blood, liver, kidney and muscle is significantly better than the amount obtained from utilizing a 1:1 leucine to zinc ration or a 2:1 leucine to zinc mixture and shows the propensity of the leucine zinc chelate to migrate to certain tissue sites.

The above examples show administration of the amino acid chelate directly into the bloodstream in order to experimentally expedite the transport of the amino acid chelate to various tissue sites. Similar results, differing only in magnitude, are obtained by the oral administration of the same products and the same comparispns can be made.

The following compositions, suitable for human oral consumption, have been formulated and are representative of the invention.

EXAMPLE VI

A zinc amino acid chelate, free of interfering anion radicals, formed by reacting three moles of lysine with one mole of zinc and having a molecular weight of about 502 was formulated with raw processed whole animal pituitary glandular materials and filled into gelatin capsules. Each capsule was formulated to contain 15 mg zinc.

EXAMPLE VII

A magnesium amino acid chelate, free of interfering anion radicals, formed by reacting two moles of tryptophan with one mole of magnesium and having a molecular weight of about 431 was formulated with raw processed whole animal brain substance and filled into gelatin capsules. Each capsule was formulated to contain 100 mg magnesium.

EXAMPLE VIII

A magnesium amino acid chelate, free of interfering anion radicals, formed by reacting two moles of methionine with one mole of magnesium and having a molecular weight of about 321 was formulated with raw processed whole animal ovarian substance and filled into gelatn capsules. Each capsule was formulated to contain 100 mg magnesium.

EXAMPLE IX

A zinc amino acid chelate, free of interfering anion radicals, formed by reacting three moles of cysteine with one mole of zinc and having a molecular weight of about 425 was formulated with raw processed whole animal brain substance and filled into gelatin capsules. Each capsule was formulated to contain 15 mg zinc.

EXAMPLE X

A zinc amino acid chelate, free of interfering anion radicals, formed by reacting three moles of glutamic acid with one mole of zinc and having a molecular weight of about 504 was formulated with raw processed liver glandular substance and filled into gelatin capsules. Each capsule was formulated to contain 15 mg zinc.

EXAMPLE XI

A zinc amino acid chelate, free of interfering anion radicals, formed by reacting three moles of arginine with one mole of zinc and having a molecular weight of about 585 was formulated with raw processed whole animal orchic glandular substance and filled into gelatin capsules. Each capsule was formulated to contain 15 mg zinc.

EXAMPLE XII

A zinc amino acid chelate, free of interfering anion radicals, formed by reacting three moles of glycine with one mole of zinc and having a molecular weight of about 291 was formulated with raw processed whole animal hypothalamus glandular substance and filled into gelatin capsules. Each capsule was formulated to contain 15 mg zinc.

EXAMPLE XIII

A manganese amino acid chelate, free of interfering anion radicals, formed by reacting three moles of glycine with one mole of manganese and having a molecular weight of about 277 was formulated with raw processed whole animal pituitary glandular substance and filled into gelatin capsules. Each capsule was formulated to contain 5 mg manganese.

EXAMPLE XIV

A manganese amino acid chelate, free of interfering anion radicals, formed by reacting three moles of methionine with one mole of manganese and having a molecular weight of about 500 was formulated with raw processed whole animal brain glandular substance and filled into gelatin capsules. Each capsule was formulated to contain 5 mg manganese.

EXAMPLE XV

A calcium amino acid chelate, free of interfering anion radicals, formed by reacting two moles of phenylalanine with one mole of calcium and having a molecular weight of about 368 was formulated with raw processed whole animal pituitary glandular substance and filled into gelatin capsules. Each capsule was formuulated to contain 200 mg calcium.

EXAMPLE XVI

A calcium amino acid chelate, free of interfering anion radicals, formed by reacting two moles of aspartic acid with one mole of calcium and having a molecular weight of about 304 was formulated with raw processed whole animal heart glandular substance and filled into gelatin capsules. Each capsule was formulated to contain 200 mg calcium.

EXAMPLE XVII

A calcium amino acid chelate, free of interfering anion radicals, formed by reacting two moles of cysteine with one mole of calcium and having a molecuar weight of about 280 was formulated with raw processed whole animal brain glandular substance and filled into gelatin capsules. Each capsule was formulated to contain 200 mg calcium.

EXAMPLE XVIII

A calcium amino acid chelate, free of interfering anion radicals, formed by reacting two moles of tryptophan with one mole of calcium and having a molecular weight of about 447 was formulated with raw processed whole animal pancreas glandular substance and filled into gelatin capsules. Each capsule was formulated to contain 100 mg calcium.

EXAMPLE XIX

A magnesium amino acid chelate, free of interfering anion radicals, formed by reacting two moles of phenylalanine with one mole of magnesium and having a molecular weight of about 353 was formulated with raw processed whole animal brain glandular substance and filled into gelatin capsules. Each capsule was formulated to contain 100 mg magnesium.

EXAMPLE XX

A magnesium amino acid chelate, free of interfering anion radicals, formed by reacting two moles of aspartic acid with one mole of magnesium and having a molecular weight of about 288 was formulated with raw processed whole animal heart substance and filled into gelatin capsules. Each capsule was formulated to contain 100 mg magnesium.

EXAMPLE XXI

An iron amino acid chelate, free of interfering anion radicals, formed by reacting two moles of glycine with one mole of iron and having a molecular weight of about 204 and a copper amino acid chelate, also free of interfering anion radicals, formed by reacting two moles of glycine with one mole of copper and having a molecular weight of about 212, were formulated with raw processed whole animal liver glandular substance and filled into gelatin capsules. Each capsule was formulated to contain 15 mg iron and 1 mg copper.

EXAMPLE XXII

An iron amino acid chelate, free of interfering anion radicals, formed by reacting two moles of glycine with one mole of iron and having a molecular weight of about 204 was formulated with raw processed whole animal liver glandular substance and filled into gelatin capsules. Each capsule was formulated to contain 15 mg iron.

EXAMPLE XXIII

A magnesium amino acid chelate, free of interfering anion radicals, formed by reacting two moles of phenylalanine with one mole of magnesium and having a molecular weight of about 353 was formulated with an herbal mixture of valerian root, passion flower, wood betony, black cohosh root, skullcap and hops and filled into elatin capsules. Each capsule was formulated to contain 100 mg magnesium.

EXAMPLE XXIV

A magnesium amino acid chelate, free of interfering anion radicals, formed by reacting two moles of aspartic acid with one mole of magnesium and having a molecular weight of about 288 was formulated with an herbal mixture of hawthorn berries, motherwort, rosemary and cayenne and filled into gelatin capsules. Each capsule was formulated to contain 100 mg magnesium.

EXAMPLE XXV

A calcium amino acid chelate, free of interfering anion radicals, formed by reacting two moles of tryptophan with one mole of calcium and having a molecular weight of about 447 was formulated with an herbal mixture of black cohosh, passion flower, comfrey root, black haw bark, saw palmetto berries, squaw vine and wild yam root and filled into gelatin capsules. Each capsule was formulated to contain 200 mg calcium.

EXAMPLE XXVI

A zinc amino acid chelate, free of interfering anion radicals, formed by reacting three moles of glycine with one mole of zinc and having a molecular weight of about 291 was formulated with an herbal mixture of pleurisy root, slippery elm bark, chickweek, comfrey, cayenne and saw palmetto berries and filled into gelatin capsules. Each capsule was formulated to contain 15 mg zinc.

EXAMPLE XXVII

A zinc amino acid chelate, free of interfering anion radicals, formed by reacting three moles of arginine with one mole of zinc and having a molecular weight of about 585 was formulated with an herbal mixture of parsley, cornsilk, bucho leaves, saw palmetto berries, cayenne and pumpkin seeds and filled into gelatin capsules. Each capsule was formulated to contain 15 mg zinc.

EXAMPLE XXVIII

A manganese amino acid chelate, free of interfering anion radicals, formed by reacting three moles of methionine with one mole of manganese and having a molecular weight of about 500 was formulated with an herbal mixture of damiana, siberian ginseng and saw palmetto and filled into gelatin capsules Each capsule was formulated to contain 5 mg manganese.

The above description, examples and formulations present a complete embodiment of the invention. However, other ligands, metals, amino acid chelates, tissue sites and the like will become obvious to one skilled in the art upon reading this specification. The the invention is deemed to cover all such embodiments within the scope of the following claims.

We claim:

1. A method of providing a bivalent metal cation to a targeted tissue site in a mammal which comprises the steps of (1) selecting a tissue site to which said bivalent metal cation is to be targeted, (2) providing said metal cation in the form of an amino acid chelate having a ligand to metal mole ratio of at least 2:1 said amino acid chelate having a molecular weight not in excess of 1500 and a stability constant of between about $10^6$ and $10^{12}$ and wherein said ligands utilized in forming said amino acid chelate are members selected from the group consisting of naturally occurring amino acids and dipeptides, tripeptides or quadrapeptides of naturally occurring amino acids said ligands being selected to provide said amino acid chelate with a propensity for being transported to said targeted tissue site and (3) administering to said mammal an effective amount of said amino acid chelate.

2. A method according to claim 1 wherein said metal cation is a member selected from the group consisting of calcium, magnesium, manganese, iron, zinc, copper, molybdenum, chromium, cobalt and selenium.

3. A method according to claim 2 wherein said ligands are members selected from the group consisting of alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine and valine and dipeptides, tripeptides and quadrapeptides formed by any combination thereof.

4. A method according to claim 3 wherein the amino acid chelate is administered orally and wherein the molecular weight of said amino acid chelate does not exceed 1000 and wherein said ligands are members selected from the group consisting of alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine and valine and dipeptides or tripeptides of any combination thereof.

5. A method according to claim 4 wherein said targeted tissue site is the brain and said metals are members selected from the group consisting of zinc, calcium and magnesium and said ligands are members selected from the group consisting of phenylalanine, tryptophan, leucine, arginine, glutamic acid tyrosine, serine, cysteine and methionine and dipeptides or tripeptides formed from any combination thereof.

6. A method according to claim 4 wherein said targeted tissue site is the hypothalamus and said metals are members selected from the group consisting of zinc and calcium and said ligands are members selected from the group consisting of glycine, glutamic acid, histidine, proline and arginine and dipeptides or tripeptides formed from any combination thereof.

7. A method according to claim 4 wherein said targeted tissue site is the pituitary and said metals are members selected from the group consisting of zinc and calcium and said ligands are members selected from the group consisting of glycine, lysine, phenylanaline, glutamic acid, histidine, proline, ornithine and arginine and dipeptides or tripeptides formed from any combination thereof.

8. A method according to claim 4 wherein said targeted tissue site is heme and said metals are members selected from the group consisting of iron and copper and said ligands are members selected from the group consisting of glycine and histidine and dipeptides or tripeptides formed from any combination thereof.

9. A method according to claim 4 wherein said targeted tissue site is the skeletel muscle and said metals are members selected from the group consisting of magnesium and calcium and said ligands are members selected from the group consisting of glycine, tryptophan, valine and arginine and dipeptides or tripeptides formed from any combination thereof.

10. A method according to claim 4 wherein said targeted tissue site is the heart and said metals are memers selected from the group consisting of iron, calcium and magnesium and said ligands are members selected from the group consisting of leucine, and aspartic acid and dipeptides or tripeptides formed from any combination thereof.

11. A method according to claim 4 wherein said targeted tissue site is the pancreas and said metals are members selected from the group consisting of zinc and calcium and said ligands are members selected from the group consisting of glycine, tryptophan, leucine and arginine and dipeptides or tripeptides formed from any combination thereof.

12. A method according to claim 4 wherein said targeted tissue site is the bones and teeth and said metals are members selected from the group consisting of magnesium and calcium and said ligands is a member-selected from the group consisting of lysine or a dipeptide or tripeptide thereof.

13. A method according to claim 4 wherein said targeted tissue site is a wound site and said metal is zinc and said ligands are members selected from the group consisting of methionine and arginine and dipeptides or tripeptides formed from any combination thereof.

14. A method according to claim 4 wherein said targeted tissue site is a male sex gland or organ and said metal is zinc and said ligands are members selected from the group consisting of glycine, and arginine and dipeptides or tripeptides formed from any combination thereof.

15. A method according to claim 4 wherein said targeted tissue site is a female sex gland or organ and said metals are members selected from the group consisting of magnesium and manganese and said ligands are members selected from the group consisting of methionine and leucine and dipeptides or tripeptides formed from any combination thereof.

16. A method according to claim 4 wherein said targeted tissue site is the liver and said metals are members selected from the group consisting of iron, zinc, copper and manganese and said ligands are members selected from the group consisting of leucine, lysine, glycine histidine, methionine, cystine, cysteine and arginine and dipeptides or tripeptides formed from any combination thereof.

17. A method according to claim 4 wherein said targeted tissue site is the kidney and said metals are members selected from the group consisting of iron, zinc, copper and manganese and said ligands are members selected from the group consisting o lysine, leucine, methionine and arginine and dipeptides or tripeptides formed from any combination thereof.

18. A method according to claim 4 wherein said targeted tissue site is the thyroid and said metals is zinc and said ligands are members selected from the group consisting of phenylanaline, glutamic acid, histidine and proline and dipeptides or tripeptides formed from any combination thereof.

19. A method according to claim 4 wherein said targeted tissue site is the skin and hair and said metal is zinc and said ligands are members selected from the group consisting of methionine, cystine, cysteine and leucine and dipeptides or tripeptides formed from any combination thereof.

20. A method according to claim 4 wherein said targeted tissue site is an enzyme system and said metal is selected from the group consisting of zinc, calcium, magnesium, manganese, iron, copper, cobalt, molybdenum and chromium and said ligand is a member selected from the group consisting of leucine and dipeptides or tripeptides thereof.

21. A method according to claim 4 wherein said targeted tissue site is a nucleic acid and said metal is magnesium and said ligands are members selected from the group consisting of glutamic acid, glutamine, glycine and aspartic acid and dipeptides or tripeptides formed from any combination thereof.

* * * * *